United States Patent [19]
Clements

[11] Patent Number: 6,033,673
[45] Date of Patent: Mar. 7, 2000

[54] DOUBLE MUTANT ENTEROTOXIN FOR USE AS AN ADJUVANT

[75] Inventor: John D. Clements, New Orleans, La.

[73] Assignee: The Administrators of Tulane Educational Fund, New Orleans, La.

[21] Appl. No.: 09/044,064

[22] Filed: Mar. 18, 1998

[51] Int. Cl.[7] .................... A61K 39/02; A61K 39/108; A61K 45/00; X61K 39/00

[52] U.S. Cl. .................... 424/236.1; 424/241.1; 424/282.1; 424/278.1; 424/184.1; 424/832; 424/9.2; 514/885

[58] Field of Search .................... 426/241.1, 236.1, 426/282.1, 278.1, 9.2, 832, 184.1; 514/885

[56] References Cited

U.S. PATENT DOCUMENTS

| | | | |
|---|---|---|---|
| 5,182,109 | 1/1993 | Tamura et al. | 424/92 |
| 5,308,835 | 5/1994 | Clements | 514/12 |

FOREIGN PATENT DOCUMENTS

| | | |
|---|---|---|
| WO 92/19265 | 11/1992 | WIPO. |
| WO 93/13202 | 7/1993 | WIPO. |

OTHER PUBLICATIONS

Cain et al. J. Biol. Chemistry 64: 329–3300, 1989.
Häse et al., 1994, "Construction and characterization of recombinant *Vibrio cholerae* strains producing inactive cholera toxin analogs", Infect. Immun. 62(8):3051–3057.
McGhee et al., 1994, "Vaccines for mucosal immunity: Unique delivery system and immune response analyses for TH1/TH2 cells and IgE/IgA B cells", Mucosal Immunology Update, Spring 1994, Raven Press, New York p. 21.

Moss et al., 1993, "Interaction of ADP–ribosylation factor with *Escherichia coli* enterotoxin that contains an inactivating lysine 112 substitution", J. Biol. Chem. 268(9):6383–6387.

Conner et al., 1993, "Rotavirus vaccine administered parenterally induces protective immunity", J. Virol. 67(11):6633–6641.

Santiago et al., 1993, "Oral immunization of rats with proteinoid microspheres encapsulating influenza virus antigens", Pharmaceutical Research 10(8):1243–1247.

Gould–Fogerite et al., 1993, In: Liposome Technology, Second Edition, vol. III, Gregoriadis (ed.), CRC Press, Boca Raton pp. 261–276.

Clements et al., 1992, In: Recombinant DNA vaccines: Rationale and Strategy, Isaacson (ed.), Marcel Decker, New York pp. 293–321.

Cardenas et al., 1992, "Oral immunization using live attenuated Salmonella spp. as carriers of foreign antigens", Clin. Microbiol. Rev. 5(3):328–342.

Lycke et al., 1992, "The adjuvant effect of *Vibrio cholerae* and *Escherichia coli* heat–labile enterotoxins is linked to their ADP–ribosyltransferase activity", Eur. J. Immunol. 22:2277–2281.

Garcon et al., 1991, "Universal vaccine carrier: Liposomes that provide T–dependent help to weak antigens", J. Immunol. 146:3697–3702.

Mowat et al., 1991 "ISCOMS—a novel strategy for mucosal immunization?", Immunol. Today 12(11):383–385.

Arai et al., 1990, "Cytokines: Coordinators of immune and inflammatory responses", Annu. Rev. Biochem. 59:783–836.

Clements et al., 1990, "Vaccines against enterotoxigenic bacterial pathogens based on the hybrid Salmonella that express heterologous antigens", Res. Microbiol. 141:981–993. Brandtzaeg, 1989, "Overview of the mucosal immune system", Curr. Top. Microbiol. Immunol. 146:13–25.

Elson, 1989, "Cholera toxin and its subunits as potential oral adjuvants", Curr. Topics Microbiol. Immunol. 146:29–33.

Liang et al., 1988, "Oral administration of cholera toxin–Sendai virus conjugate potentiates gut and respiratory immunity against Sendai virus", J. Immunol. 141(5):1495–1501.

Clemens et al., 1988, "Cross–protection by B subunit–whole cell cholera vaccine against diarrhea associated with heat–labile toxin–producing enterotoxigenic *Escherichia coli:* Results of a large–scale field trial", J. Infect. Dis. 158(2):372–377.

Clements et al., 1988, "Adjuvant activity of *Escherichia coli* heat–labile enterotoxin and effect on the induction of oral tolerance in mice to unrelated protein antigens", Vaccine 6:269–277.

Clements et al., 1988, "*Escherichia coli* heat–labile enterotoxin possesses adjuvant activity and prevents the induction of oral tolerance in mice to unrelated protein antigens", Abstract No. B–91, 88th Ann. Meet. Am. Soc. Microbiol.

Alving et al., 1986, "Effectiveness of liposomes as potential carriers of vaccines: Applications to cholera toxin and human malaria sporozoite antigen", Vaccine 4:166–172.

Owen et al., 1986, "M cell transport of *Vibrio cholerae* from the intestinal lumen into Peyer's patches: A mechanism for antigen sampling and for microbial transepithelial migration", J. Infect. Dis. 153(6):1108–1118.

Lycke et al., 1986, "Strong adjuvant properties of cholera toxin on gut mucosal immune responses to orally presented antigens", Immunology 59:301–308.

Cebra et al., 1986, In: Vaccines 86, Brown et al. (eds.), Cold Spring HArbor Laboratory, New York pp. 129–133.

Elson et al., 1984, "Cholera toxin feeding did not induce oral tolerance in mice and abrogated oral tolerance to an unrelated protein antigen", J. Immunol. 133(6):2892–2897.

(List continued on next page.)

*Primary Examiner*—James C. Housel
*Assistant Examiner*—S. Devi
*Attorney, Agent, or Firm*—Pennie & Edmonds LLP

[57] ABSTRACT

The present invention is directed towards a novel composition which is a genetically distinct mutant of *E. coli* heat-labile enterotoxin (LT). Specifically, the mutant LT designated LT(R192G/L211A) is modified by two amino acid substitutions, i.e., the arginine at amino acid position 192 is replaced by glycine and the leucine at amino acid position 211 is replaced by alanine. The invention relates to compositions and methods for use of the novel double mutant of LT as an adjuvant.

19 Claims, 8 Drawing Sheets

OTHER PUBLICATIONS

Clements et al., 1984, "Construction of a potential live oral bivalent vaccine for typhoid fever and cholera–*Escherichia coli*–related diarrheas", Infect. Immun. 46(2):564–569.

Strober et al., 1985, In: Advances in host defense mechanisms, vol. 4., Mucosal Immunity, Gallin and Fauci (eds.), Raven Press, New York, pp. 1–30.

Tomasi et al., 1985, In: Advances in host defense mechanisms, vol. 4., Mucosal Immunity, Gallin and Fauci (eds.), Raven Press, New York, pp. 31–61.

McKenzie et al., 1984, Cholera toxin B subunit as a carrier protein to stimulate mucosal immune response, J. Immunol. 133(4):1818–1824.

Elson et al., 1984, "Generalized systemic and mucosal immunity in mice after mucosal stimulation with cholera toxin", J. Immunol. 132(6):2736–2741.

Svennerholm et al., 1984, "Mucosal antitoxic and antibacterial immunity after cholera disease and after immunization with a combined B subunit–whole cell vaccine", J. Infect. Dis. 149(6):884–893.

Pierce et al., 1983, "Procholeragenoid: A safe and effective antigen for oral immunization against experimental cholera", Infect. Immun. 40(3):1112–1118.

Clements et al., 1983, "Cloning and molecular characterization of the B subunit of *Escherichia coli* heat–labile enterotoxin", Infect. Immun. 40(2):653–658.

Dallas et al., 1980, "Amino acid sequence homology between cholera toxin and *Escherichia coli* heat–labile toxin", Nature 288:499–501.

Clements et al., 1980, "Properties of homogenous heat–labile enterotoxin from *Escherichia coli*", Infect. Immun. 29:91–97.

Field, 1980, In: Secretory diarrhea, Field et al., (eds.) Waverly Press, Baltimore, pp. 21–30.

Clements et al., 1979, "Isolation and characterizaton of homogenous heat–labile enterotoxins with high specific activity from *Escherichia coli* cultures", Infect. Immun. 24:760–769.

Clements et al., 1979, "Demonstration of shared and unique immunological determinants in enterotoxins from *Vibrio cholerae* and *Escherichia coli*", Infect. Immun. 22:709–713.

Clements et al., 1978, "Immunological cross–reactivity between a heat–enterotoxin(s) of *Escherichia coli* and subunits of *Vibrio cholerae* enterotoxin", Infect. Immun. 21:1036–1039.

Finkelstein, 1975, "Immunology of cholera", Curr. Top. Microbiol. Immunol. 69:139–196.

Bockman et al., 1973, "Pinocytosis by epithelium associated with lymphoid follicles in the bursa of fabricius, appendix, and Peyer's patches. An electron microscope study", Am. J. Anat. 136:455–477.

Finkelstein and LoSpalluto, 1969, "Pathogenesis of experimental cholera: Preparation and isolation of choleragen and choleragenoid", J. Exp. Med. 130:185–202.

Douce et al., 1995, "Mutants of *Escherichia coli* heat–labile toxin lacking ADP–ribosyltransferase activity act as nontoxic, mucosal adjuvants," Proc. Natl. Acad. Sci. 92:1644–1648.

Lobet et al., 1991, "Effect of site–directed mutagenic alterations on ADP–ribosyltransferase activity of the A subunit of *Escherichia coli* heat–labile enterotoxin," Infection and Immunity 59(9):2870–2879.

Burnette et al., 1991, "Site–specific mutagenesis of the catalytic subunit of cholera toxin: Substituting lysine for arginine 7 causes loss of activity," Infection and Immunity 59(11):4266–4270.

Okamoto et al., 1988, "Effect of substitution of glycine for arginine at position 146 of the A1 subunit on biological activity of *Escherichia coli* heat–labile enterotoxin," J. Bacteriol. 170(5):2208–2211.

Cherwinski et al., 1987, Two Types of Mouse Helper T Cell Clone III. Further Differences in Lymphokine Synthesis between Th1 and Th2 Clones Revealed by RNA hybridization, Functionally Monospecific Bioassays, and Monoclonal Antibodies, J. Exp. Med. 166:1229–1244.

Di Tommaso, 1996, "Induction of Antigen–Specific Antibodies in Vaginal Secretions by Using a Nontoxic Mutant of Heat–Labile Enterotoxin as a Mucosal Adjuvant" Infection and Immunity 64(3):974–979.

Dickinson et al., 1995, "Dissociation of *Escherichia coli* Heat–Labile Enterotoxin Adjuvanticity from ADP–Ribosyltransferase Activity," Infection and Immunity 63(5):1617–1623.

Dickinson et al., 1996, "Use of *Escherichia coli* Heat–Labile Enterotoxin as an Oral Adjuvant," Mucosal Vaccines pp. 73–87.

Domenighini et al., 1994, "Common features of the NAD–binding and catalytic site of ADP–ribosylating toxins," Molecular Microbiology 14(1):41–50.

Douce et al., 1997, "Intranasal Immunogenicity and Adjuvanticity of Site–Directed Mutant Derivatives of Cholera Toxin," Infection and Immunity 65(7):2821–2828.

Good, 1992, "A malaria vaccine strategy based on the induction of cellular immunity," Immunology Today 13(4):126–130.

Grant et al., 1994, "Role of Trypsin–Like Cleavage at Arginine 192 in the Enxymatic and Cytotonic Activities of *Escherichia coli* Heat–Labile Enterotoxin," Infection and Immunity 62(10):4270–4278.

Harford et al., 1989, "Inactivation of the *Escherichia coli* heat–labile enterotoxin by in vitro mutagenesis of the A–subunit gene," Eur. J. Biochem. 183:311–316.

Hashigucci et al., 1996, "Antibody responses in volunteers induced by nasal influenza vaccine combined with *Escherichia coli* heat–labile enterotoxin B subunit containing a trace amount of the holotoxin," Vaccine 14(2):113–119.

Hathaway et al., 1995, "Induction of systemic immune responses to measles virus synthetic peptides administered intranasally," Vaccine 13(16):1495–1500.

Holmgren et al., 1994, "Strategies for the Induction of Immune Responses at Mucosal Surfaces Making Use of Cholera Toxin B Subunit as Immunogen, Carrier, and Adjuvant," Am. J. Trop. Med. Hyg. 50(5)Suppl. 42–54.

Holmgren et al., 1993, "Cholera toxin and cholera–B subunit as oral mucosal adjuvant and antigen vector systems," Vaccine 11(12):1179–1184.

Katz et al., 1996, "Heat–labile enterotoxin from *Escherichia coli* as an adjuvant for oral influenza vaccination," Options for the control of influenza III, L.E. Brown, A.W. Hampson and R.G. Webst er, editors, pp. 292–297.

Katz et al., 1997, "Adjuvant–Activity of the Heat–Labile Enterotoxin from Enterotoxigenic *Escherichia coli* for Oral Administration of Invactivated Influenza Virus Vaccine," The Journal of Infectious Diseases 175:352–63.

Lai, Bacterial Protein Toxins with Latent ADP–Ribosyl Transferases Activities, pp. 99–140, 1986.

Lee, 1995, "Oral immunization with Recombinant *Helicobacter pylori* Urease Induces Secretory IgA Antibodies and Protects Mice from Challenge with *Helicobater felis*," The Journal of Infectious Diseases. 172:161–72.

Levine et al., 1983, "New Knowledge on Pathogenesis of Bacterial Enteric Infections as Applied to Vaccine Development," Microbiological Reviews, 47(4):510–550.

Loosmore et al., 1990, "Engineering of Genetically Detoxified Pertussis Toxin Analogs for Development of a Recombinant Whooping Cough Vaccine," Infection and Immunity 58(11):3653–3662.

McGhee et al., 1993, "New Perspectives in Vaccine Development: Mucosal Immunity to Infection," Infectious Agents and Disease 2:55–73.

Merritt et al., 1995, "Mutation of a buried residue causes loss of activity but no conformational change in the heat–labile enterotoxin of *Escherichia coli*," Structural Biology 2(4):269–272.

Mosmann et al., 1989, "TH1 and TH2 Cells: Different Patterns of Lymphokine Secretion Lead to Different Functional Properties," Ann. Rev. Immunol. 7:145–73.

Pizza et al., 1994, "Probing the structure–activity relationship of *Escherichia coli* LT–A by site–directed mutagenesis," Molecular Microbiology 14(1):51–60.

Sixma et al., 1991, "Crystal structure of a cholera toxin–related heat–labile enterotoxin from *E. coli*," Nature 351:371–377.

Sixma et al., 1993, "Refined Structure of *Escherichia coli* Heat–labile Enterotoxin, a Close Relative of Cholera Toxin," J. Mol. Biol. 230:890–918.

Staats et al., 1996, "Systemic and Vaginal Antibody Responses After Intranasal Immunization with the HIV–1 C4/V3 Peptide T1SP10 MN(A)," The Journal of Immunology pp. 462–472.

Tsuji et al., 1991, "Glutamic acid–112 of the A subunit of heat–labile enterotoxin from enterotoxigenic *Escherichia coli* is important for ADP–ribosyltransferase activity," FEBS Letters 291(2):319–321.

Tsuji et al., 1997, "Relationship between a low toxicity of the mutant A subunit of enterotoxigenic *Escherichia coli* enterotoxin and its strong adjuvant action," Immunology 9:176–182.

Tsuji et al., 1990, "A Single Amino Acid Substitution in the A Subunit of *Escherichia coli* Enterotoxin Results in a Loss of Its Toxic Activity," The Journal of Biological Chemistry 265(36):22520–22525.

Urban Jr. et al., 1992, "The Importance of Th2 Cytokines in Protective Immunity to Nematodes," Immunological Reviews 127:205–220.

Weltzin et al., 1997, "Novel intranasal immunization techniques for antibody induction and protection of mice against gastric *Helicobacter felis* infection," Vaccine 15(4):370–376.

Wu et al., 1997, "Intranasal Immunization of Mice with PspA (Pneumococcal Surface Protein A) Can Prevent Intranasal Carriage, Pulmonary Infection, and Sepsis with *Streptococcus pneumoniae*," The Journal of Infectious Diseases 175:839–46.

Xu–Amano et al., 1993, "Helper T Cell Subsets for Immunoglobulin A Responses: Oral Immunization with Tetanus Toxoid and Cholera Toxin as Adjuvant Selectively Induces Th2 Cells in Mucosa Associated Tissues," J. Exp. Med. 178:1309–1320.

Xu–Amano et al., 1996, "Helper Th1 and Th2 Cell responses following mucosal or systemic immunization with cholera toxin," Vaccine 14:113–119.

Yamamoto et al., 1996, "The Role of Th1 and Th2 Cells for Mucosal IgA Responses," Annals of the New York Academy of Sciences 778:64–71.

Yamamoto et al., 1997, "Mutants in the ADP–ribosyltransferase Cleft of Cholera Toxin Lack Diarrheagenicity but Retain Adjuvanticity," J. Exp. Med. 185(7):1203–1210.

Yamamoto et al., 1997, "A nontoxic mutant of cholera toxin elicits Th2–type responses for enhanced mucosal immunity," Proc. Natl. Acad. Sci. USA 94:5267–5272.

```
                187                         192
                TGT GGA AAT TCA TCA AGA ACA ATT ACA GGT GAT ACT TGT AAT
                Cys Gly Asn Ser Ser Arg Thr Ile Thr Gly Asp Thr Cys Asn 211         214
                GAG GAG ACC CAG AAT CTG AGC ACA ATA TAT CTC AGG AAA TAT
                Glu Glu Thr Gln Asn Leu Ser Thr Ile Tyr Leu Arg Lys Thr
```

FIG.2

| Lane | Sample |
|---|---|
| 1 | Marker |
| 2 | LT |
| 3 | LT + Trypsin |
| 4 | LT(R192G) |
| 5 | LT(R192G) + Trypsin |
| 6 | LT(L211A) |
| 7 | LT(L211A) + Trypsin |
| 8 | LT(R192G/L211A) |
| 9 | LT(R192G/L211A) + Trypsin |

FIG.3A

| Lane | Sample |
|---|---|
| 1 | Marker |
| 2 | LT |
| 3 | LT + Pepsin |
| 4 | LT(R192G) |
| 5 | LT(R192G) + Pepsin |
| 6 | LT(L211A) |
| 7 | LT(L211A) + Pepsin |
| 8 | LT(R192G/L211A) |
| 9 | LT(R192G/L211A) + Pepsin |

DOUBLE MUTANT ENTEROTOXIN FOR USE AS AN ADJUVANT

TABLE OF CONTENTS

1. FIELD OF THE INVENTION
2. BACKGROUND OF THE INVENTION
2.1. MUCOSAL ADJUVANTS
3. SUMMARY OF THE INVENTION
4. BRIEF DESCRIPTION OF THE FIGURES
5. DETAILED DESCRIPTION OF THE INVENTION
5.1 LT(R192G/L211A) AND COMPOSITIONS THEREOF
5.2 PRODUCTION OF LT(R192G/L211A)
   5.2.1 MODE OF ADMINISTRATION OF LT(R192G/L211A) AND UNRELATED ANTIGENS
5.3 ANTIGENS USEFUL IN THE INVENTION
6. EXAMPLES
6.1. CONSTRUCTION OF LT(R192G/L211A)
6.2. LT(R192G/L211A) EXHIBITS RESISTANCE TO PEPSIN CLEAVAGE
6.3. ENTEROTOXICITY IN THE PATEN MOUSE ASSAY
6.4. INTRANASAL ADJUVANTICITY OF LT(R192G/L211A)
7. DEPOSIT OF PLASMIDS

1. FIELD OF THE INVENTION

The present invention is directed towards a novel composition which is a genetically distinct mutant of *E. coli* heat-labile enterotoxin (LT). Specifically, the mutant LT designated LT(R192G/L211A) is modified by two amino acid substitutions, i.e., the arginine at amino acid position 192 is replaced by glycine and the leucine at amino acid position 211 is replaced by alanine. The invention relates to compositions and methods for use of the novel double mutant of LT as an adjuvant.

2. BACKGROUND OF THE INVENTION

The World Health Organization report of Infectious Disease deaths for 1995 indicated that there were more than 13 million deaths world-wide during that year. The majority of those deaths were caused by organisms that first make contact with and then either colonize or cross mucosal surfaces to infect the host. The overall morbidity caused by these organisms and other pathogens that interact with mucosal surfaces is impossible to calculate.

Traditional vaccine strategies that involve parenteral immunization with inactivated viruses or bacteria or subunits of relevant virulence determinants of those pathogens do not prevent those interactions. In fact, traditional vaccine strategies do not prevent infection but instead resolve infection before disease ensues. In some cases, HIV for example, once the virus crosses the mucosal surface and enters the host cell, be that a dendritic cell, an epithelial cell, or a T-cell, the host-parasite relationship is moved decidedly in favor of the parasite (HIV). In that case, as in many others, a vaccine strategy that does not prevent the initial infection of the host is unlikely to succeed.

Recently, a great deal of attention has focused on mucosal immunization as a means of inducing secretory IgA (sIgA) antibodies directed against specific pathogens of mucosal surfaces. The rationale for this is the recognition that sIgA constitutes greater than 80% of all antibodies produced in mucosal-associated lymphoid tissues in humans and that sIgA may block attachment of bacteria and viruses, neutralize bacterial toxins, and even inactivate invading viruses inside of epithelial cells. In addition, the existence of a Common Mucosal Immune System permits immunization on or at one mucosal surface to induce secretion of antigen-specific sIgA at distant mucosal sites. It is only now being appreciated that mucosal immunization may be an effective means of inducing not only sIgA but also systemic antibody and cell-mediated immunity.

The mucosal immune response can be divided into two phases (McGhee and Kiyono, 1993, *Infect Agents Dis* 12:55–73). First, the inductive phase involves antigen presentation and the initiation events which dictate the subsequent immune response. During the initiation events, antigen-specific lymphocytes are primed and migrate from the inductive sites (e.g., Peyer's patches in the enteric mucosa) through the regional lymph nodes, into the circulation and back to mucosal effector sites (e.g., lamina propria). Once these effector cells have seeded their effector sites, the second phase, or effector phase, of the mucosal immune response can occur. A significant difference between mucosal immunization and parenteral immunization is that both mucosal and systemic immunity can be induced by mucosal immunization while parenteral immunization generally results only in systemic responses.

Most studies conducted to date have dealt with the secretory antibody component of the mucosal response and the complex regulatory issues involved with induction of sIgA following mucosal immunization and not with the systemic antibody response or cellular immunity induced by mucosal immunization. In that regard, it is important to understand the type of helper T lymphocyte response induced by mucosal immunization since the type of helper T lymphocyte stimulated by an antigen is one of the most important factors for defining which type of immune response will follow. Mosmann and colleagues (Cherwinski et al., 1987, *Journal of Experimental Medicine* 166:1229–1244; Mosmann and Coffman, 1989, *Annual Reviews of Immunology* 7:145–173) discovered that there are at least two different types of helper T lymphocytes (Th) which can be identified based on cytokine secretion. Th1 lymphocytes secrete substantial amounts of IL-2 and INF-gamma and execute cell-mediated immune responses (e.g., delayed type hypersensitivity and macrophage activation), whereas Th2 lymphocytes secrete IL-4, IL-5, IL-6 and IL-10 and assist in antibody production for humoral immunity. Theoretically then, antigenic stimulation of one T helper cell subset and not the other would result in production of a particular set of cytokines which would define the resulting immune response.

The presence of IL-2 and INF-gamma coupled with an antigenic stimulus presented by macrophages in the context of Class II MHC molecules can initiate Th1 type responses. The ability of Th1 cells to secrete IL-2 and INF-gamma further amplifies the response by activating Th1 cells in an autocrine fashion and macrophages in a paracrine fashion. These activated leukocytes can release additional cytokines (e.g., IL-6) which may induce the proliferation and differentiation of antigen specific B lymphocytes to secrete antibody (the effector phase). In this scenario, the predominant isotype secreted by murine B lymphocytes is often IgG2a. In a second scenario (Urban et al., 1992, *Immunol Rev* 127:205–220), antigens such as allergens or parasites can effectively stimulate a Th2 lymphocyte response (the inductive phase). Presentation of such antigens to Th2 cells can result in the production of the lymphokines IL-4 and IL-5 which can induce antigen specific B lymphocytes to secrete IgE and IgG1 or induce eosinophillia, respectively (the effector phase). Furthermore, stimulated Th2 cells can secrete IL-10 which has the ability to specifically inhibit secretion of IL-2 and INF-gamma by Th1 lymphocytes and also to inhibit macrophage function.

While these representations are simplistic, it is obvious that the type of T helper cell stimulated affects the resultant cellular immune response as well as the predominant immunoglobulin isotype secreted. Specifically, IL-4 stimulates switching to the IgE and IgG1 isotypes whereas INF-gamma stimulates IgG2a secretion. Numerous studies, predominantly conducted in vitro, have suggested that IL-5, IL-6 and TGF-beta (Th3) can cause isotype switching to IgA.

2.1. Mucosal Adjuvants

Mucosally administered antigens are frequently not immunogenic. A number of strategies have been developed to facilitate mucosal immunization, including the use of attenuated mutants of bacteria (e.g., Salmonella spp.) as carriers of heterologous antigens, encapsulation of antigens into microspheres, gelatin capsules, different formulations of liposomes, adsorption onto nanoparticles, use of lipophilic immune stimulating complexes, and addition of bacterial products with known adjuvant properties. The two bacterial products with the greatest potential to function as mucosal adjuvants are cholera toxin (CT), produced by various strains of *Vibrio cholerae,* and the heat-labile enterotoxin (LT) produced by some enterotoxigenic strains of *Escherichia coli* (Clements et al., 1988, Vaccine 6:269–277; Elson, 1989, *Immunology Today* 146:29–33; Lycke et al., 1992, *European Journal of Immunology* 22:2277–2281; Xu-Amano et al., 1993, *Journal of Experimental Medicine* 178:1309–1320; Yamamoto et al., 1996, *Annals of the New York Academy of Sciences* 778:64–71).

Although LT and CT have many features in common, these are clearly distinct molecules with biochemical and immunologic differences which make them unique (see below). Both LT and CT are synthesized as multisubunit toxins with A and B components. On thiol reduction, the A component dissociates into two smaller polypeptide chains. One of these, the A1 piece, catalyzes the ADP-ribosylation of the stimulatory GTP-binding protein (GSa) in the adenylate cyclase enzyme complex on the basolateral surface of the epithelial cell resulting in increasing intracellular levels of cAMP. The resulting increase in cAMP causes secretion of water and electrolytes into the small intestine through interaction with two cAMP-sensitive ion transport mechanisms involving 1) NaCl cotransport across the brush border of villous epithelial cells, and 2) electrogenic Na dependent Cl secretion by crypt cells (Field, 1980, *Secretory Diarrhea* pp21–30). The B-subunit binds to the host cell membrane receptor (ganglioside GM1) and facilitates the translocation of the A-subunit through the cell membrane.

Recent studies have examined the potential of CT and LT as a mucosal adjuvant against a variety of bacterial and viral pathogens using whole killed organisms or purified subunits of relevant virulence determinants from these organisms. Representative examples include tetanus toxoid (Xu-Amano et al., 1993, *Journal of Experimental Medicine* 178:1309–1320; Yamamoto et al., 1996, *Annals of the New York Academy of Sciences* 778:64–71; Xu-Amano et al., 1994, *Vaccine* 12:903–911), inactivated influenza virus (Hashigucci et al., 1996, *Vaccine* 14:113–119; Katz et al., 1996, *Options for the control of influenza.* III., pp292–297; Katz et al., 1997, *Journal of Infectious Diseases* 175:352–363), recombinant urease from Helicobacter spp. (Lee et al., 1995, *Journal of Infectious Diseases* 172:161–171; Weltzin et al., 1997, *Vaccine* 4:370–376), pneumococcal surface protein A from *Streptococcus pneumoniae* (Wu et al., 1997, *Journal of Infectious Diseases* 175:839–846), Norwalk virus capsid protein, synthetic peptides from measles virus (Hathaway et al., 1995, *Vaccine* 13:1495–1500), and the HIV-1 C4/V3 peptide T1SP10 MN(A) (Staats et al., 1996, *Journal of Immunology* 157:462–472). There are many other examples and it is clear that both LT and CT have significant potential for use as adjuvants for mucosally administered antigens (see Dickinson and Clements, 1996, *Mucosal Vaccines pp.*73–87 for a recent review). This raises the possibility of an effective immunization program against a variety of pathogens involving the mucosal administration of killed or attenuated agents or relevant virulence determinants of specific agents in conjunction with LT or CT. However, the fact that these "toxins" can stimulate a net lumenal secretory response may prevent their use. For instance, as little as 5 μg of purified CT was sufficient to induce significant diarrhea in volunteers while 25 μg was shown to elicit a full 20-liter cholera purge (Levine et al., 1983, *Microbiological Reviews* 47:510–550). In recently conducted volunteer studies with LT administered alone or in conjunction with the *V. cholerae* Whole Cell/B-Subunit Vaccine, LT was shown to induce fluid secretion at doses as low as 2.5 μg when administered in conjunction with the vaccine, while 25 μg of LT elicited up to 6-liters of fluid. While the adjuvant effective dose in humans for either of these toxins has not been established, experiments in animals suggest that it may be a comparable to the toxic dose. Taken together, these studies indicate that while LT and CT may be attractive as mucosal adjuvants, studies in animals do not reflect the full toxic potential of these molecules in humans, and that toxicity will seriously limit their practical use for humans.

A number of attempts have been made to alter the toxicity of LT and CT, most of which have focused on eliminating enzymatic activity of the A-subunit associated with enterotoxicity. The majority of these efforts have involved the use of site-directed mutagenesis to change amino acids associated with the crevice where NAD binding and catalysis is thought to occur. Recently, a model for NAD binding and catalysis was proposed (Domenighini et al., 1994, *Molecular Microbiology* 14:41–50; Pizza et al., 1994, *Molecular Microbiology* 14:51–60) based on computer analysis of the crystallographic structure of LT (Sixma et al., 1991, *Nature (London)* 351:371–377; Sixma et al., 1993, *Journal of Molecular Biology* 230:890–918). Replacement of any amino acid in CT or LT involved in NAD-binding and catalysis by site-directed mutagenesis has been shown to alter ADP-ribosyltransferase activity with a corresponding loss of toxicity in a variety of biological assay systems (Lycke et al., 1992, *European Journal of Immunology* 22:2277–2281; Burnette et al., 1991, *Infection and Immunity* 59:4266–4270; Harford et al., 1989, *European Journal of Biochemistry* 183:311–316; Hase et al., 1994, *Infection and Immunity* 62:3051–3057; Lobet et al., 1991, *Infection and Immunity* 59:2870–2879; Merritt et al., 1995, *Nature Structural Biology* 2:269–272; Moss et al., 1993, *Journal of Biological Chemistry* 268:6383–6387; Tsuji et al., 1991, FEBS Letters 291:319–321; Tsuji et al., 1990, *Journal of Biological Chemistry* 265:22520–22525). In addition, it has been shown that exchanging K for E112 in LT not only removes ADP-ribosylating enzymatic activity, but cAMP activation and adjuvant activity as well (Lycke et al., 1992, *European Journal of Immunology* 22:2277–2281). A logical conclusion from the Lycke et al. studies was that ADP-ribosylation and induction of cAMP are essential for the adjuvant activity of these molecules. As a result, a causal linkage was established between adjuvanticity and enterotoxicity. That is, the accumulation of cAMP responsible for net ion and fluid secretion into the gut lumen was thought to be a requisite to adjuvanticity. Recent studies by a number of laboratories have challenged that linkage.

Dickinson and Clements (Dickinson and Clements, 1995, *Infection and Immunity* 63:1617–1623) (Clements et al.) explored an alternate approach to dissociation of enterotoxicity from adjuvanticity. LT requires proteolysis of a trypsin sensitive bond to become fully active. In this enterotoxin, that trypsin sensitive peptide is subtended by a disulfide interchange that joins the A1 and A2 pieces of the A-subunit. In theory, if the A1 and A2 pieces cannot separate, A1 will not be able to find its target (adenylate cyclase) on the basolateral surface or assume the conformation necessary to bind or hydrolyze NAD.

The mutant of Clements et al. has been described more fully in PCT Publication WO96/06627, incorporated herein by reference. The mutant LT holotoxin, designated LT(R192G), was constructed using site-directed mutagenesis to create a single amino acid substitution within the disulfide subtended region of the A-subunit separating A1 from A2. This single amino acid change altered the proteolytically sensitive site within this region, rendering the mutant insensitive to trypsin activation. The physical characteristics of this mutant were examined by SDS-PAGE, its biological activity was examined on mouse Y-1 adrenal tumor cells and Caco-2 cells, its enzymatic properties determined in an in vitro NAD:agmatine ADP-ribosyltransferase assay, and its immunogenicity and immunomodulating capabilities determined by testing for the retention of immunogenicity and adjuvanticity.

Properties of LT(R192G)

100–1,000 fold less active than cholera toxin or native LT in the mouse Y-1 adrenal cell assay Not sensitive to proteolytic activation Does not possess in vitro NAD:agmatine ADP-ribosyltransferase activity Does not increase production of cAMP in cultured Caco-2 cells Reduced enterotoxicity in the patent mouse intestinal challenge model when compared to native LT Promotes the development of both humoral (antibody) and cell-mediated immune responses against co-administered antigens of a pathogenic microorganism in both the systemic and mucosal compartments Functions as an effective adjuvant when administered mucosally (i.e., orally, intranasally) or parenterally (i.e., subcutaneously)

Lacks enterotoxicity in humans at adjuvant-effective doses

LT(R192G) has been shown to possess the capability of enhancing an immune response (e.g., IgG, IgA) to antigens unrelated to LT or LT(R192G). Recent experimental evidence shows that LT(R192G) has utility as an adjuvant for mucosally or parenterally administered antigens; such administration results in the production of serum IgG and/or mucosal sIgA as well as cell-mediated immune responses against the antigen with which LT(R192G) is delivered and, more importantly, to protect against subsequent challenge with infectious organisms. LT(R192G) has been shown to be an effective mucosal adjuvant and has recently been evaluated in humans in several Phase I safety studies.

More recently, Tsuji et al. (Tsuji et al., 1997, *Immunology* 90:176–182) demonstrated that a protease-site deletion mutant LT(Δ192–194) also lacks in vitro ADP-ribosylagmatine activity, has a ten-fold reduction in enterotoxicity in rabbit ligated ileal loops, and a 50% reduction and delayed onset of cAMP induction in cultured myeloma cells. LT(A192–194) was shown to have increased adjuvant activity for induction of serum IgG and mucosal IgA against measles virus when compared to native LT, LT-B, or LT(E112K). LT(A192–194) was effective when administered intranasally, subcutaneously, intraperitoneally, or orally although mucosal IgA responses were only demonstrated following mucosal administration. These investigators also demonstrated increased adjuvant activity for mucosally administered LT(Δ192–194) in conjunction with KLH, BCG, and Ova. These findings are consistent with the findings with LT(R192G).

3. SUMMARY OF THE INVENTION

The present invention provides a new mutant LT molecule containing one additional mutation of leucine at position 211 to alanine (L211A).

More particularly, the present invention provides a novel LT molecule, LT(R192G/L211A), which exhibits the adjuvanticity of LT(R192G), but which surprisingly has even lower enterotoxicity compared to a large dose of LT(R192G) holotoxin. See, for example, FIG. 4. It has been noted that 250 μg of LT(R192G) has less enterotoxicity in the patent mouse assay than does 5 μg of native LT. The novel double mutant LT(R192G/L211A) has even less enterotoxicity than does LT(R192G) in the patent mouse assay.

Also provided are methods of using LT(R192G/L211A) as an adjuvant for the stimulation of an immune response against an antigen administered in combination with the novel adjuvant.

LT(R192G) has previously been shown to possess the capability of enhancing an immune response (e.g., IgG, IgA) to antigens unrelated to LT or LT(R192G). Recent experimental evidence shows that LT(R192G) has utility as an adjuvant for mucosally or parenterally administered antigens; such administration results in the production of serum IgG and/or mucosal sIgA as well as cell-mediated immune responses against the antigen with which LT(R192G) is delivered and, more importantly, to protect against subsequent challenge with infectious organisms.

Figure 4:
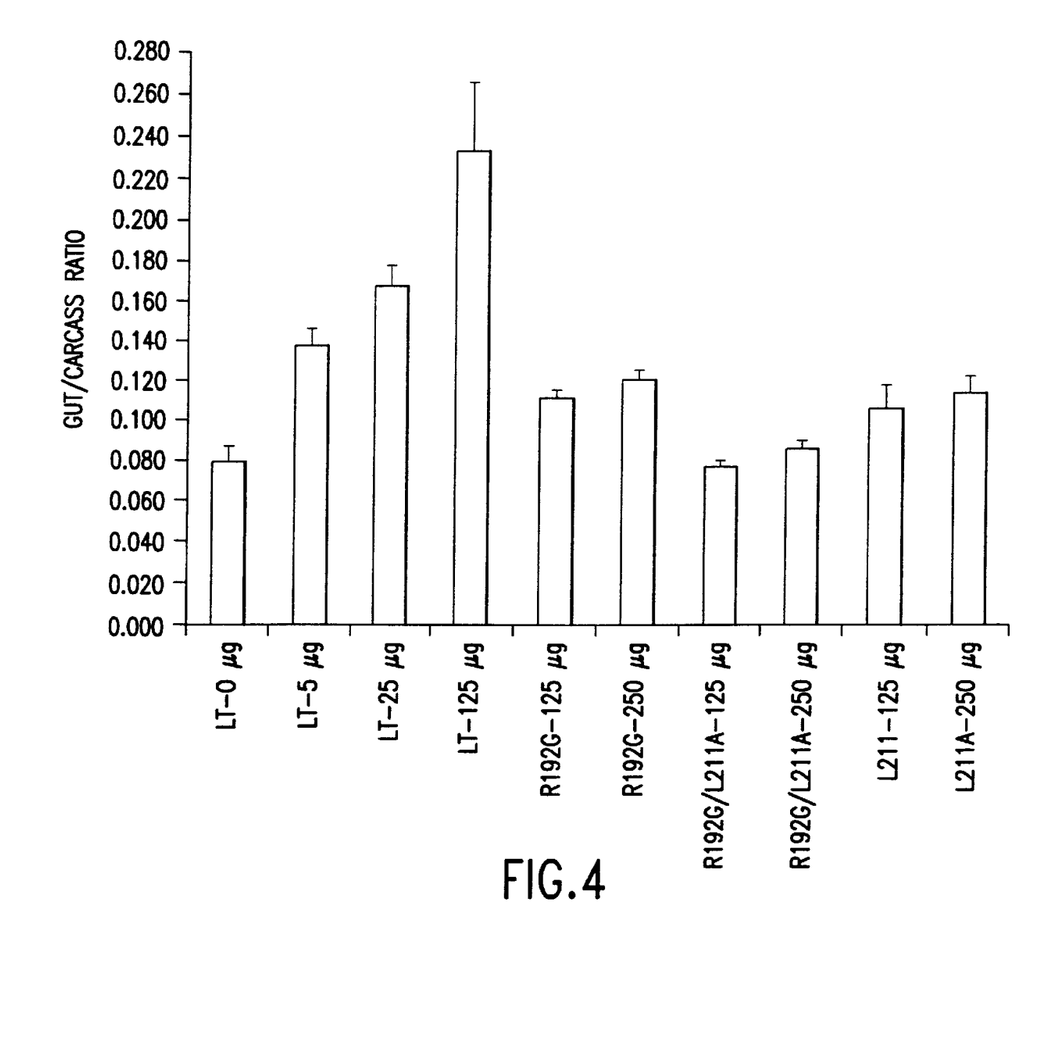
FIG. 4 shows a patent mouse intestinal assay demonstrating that LT(R192G/L211A) has lower toxicity than an equivalent amount of LT(R192G). For these studies, LT(R192G) and LT(R192G/L211A) were examined for enterotoxicity in the patent mouse assay. Groups of mice were orally inoculated with native LT at 5, 25, or 125 µg, or with LT(R192G/L211A) at 125 or 250 µg, or with LT(R192G) at 25, 125, or 250 µg. Following a three hour interval, the gut:carcass ratio of each animal was determined. The gut-carcass ratio is defined as the intestinal weight divided by the remaining carcass weight. There were three animals per group and the means for each data point are shown.
Figure 5:
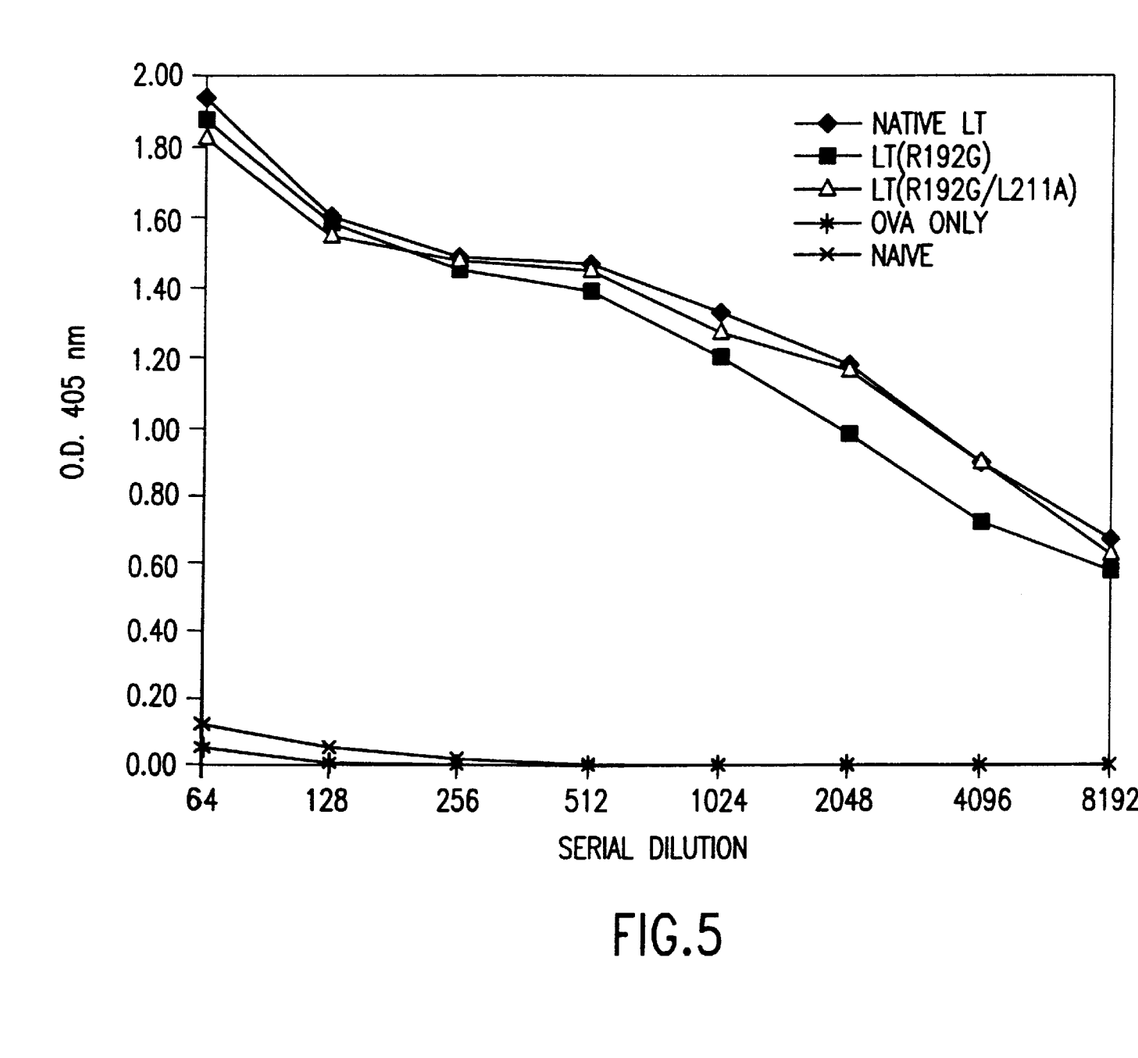
FIG. 5 demonstrates that LT(R192G/L211A) functions equally as well as LT(R192G) as an immunologic adjuvant for induction of serum IgG when administered intranasally. Mice were immunized intranasally with Ovalbumin (Ova) alone or in conjunction with 5 µg of LT(R192G/L211A), LT(R192G), or native LT. Serum anti-Ova IgG was determined by ELISA. There were seven animals per group and the means for each data point are shown. Mice immunized intranasally with Ova in conjunction with LT(R192G) had serum anti-Ova IgG responses indistinguishable from animals immunized with Ova in conjunction with LT(R192G/L211A) or in conjunction with native LT.
Figure 6:
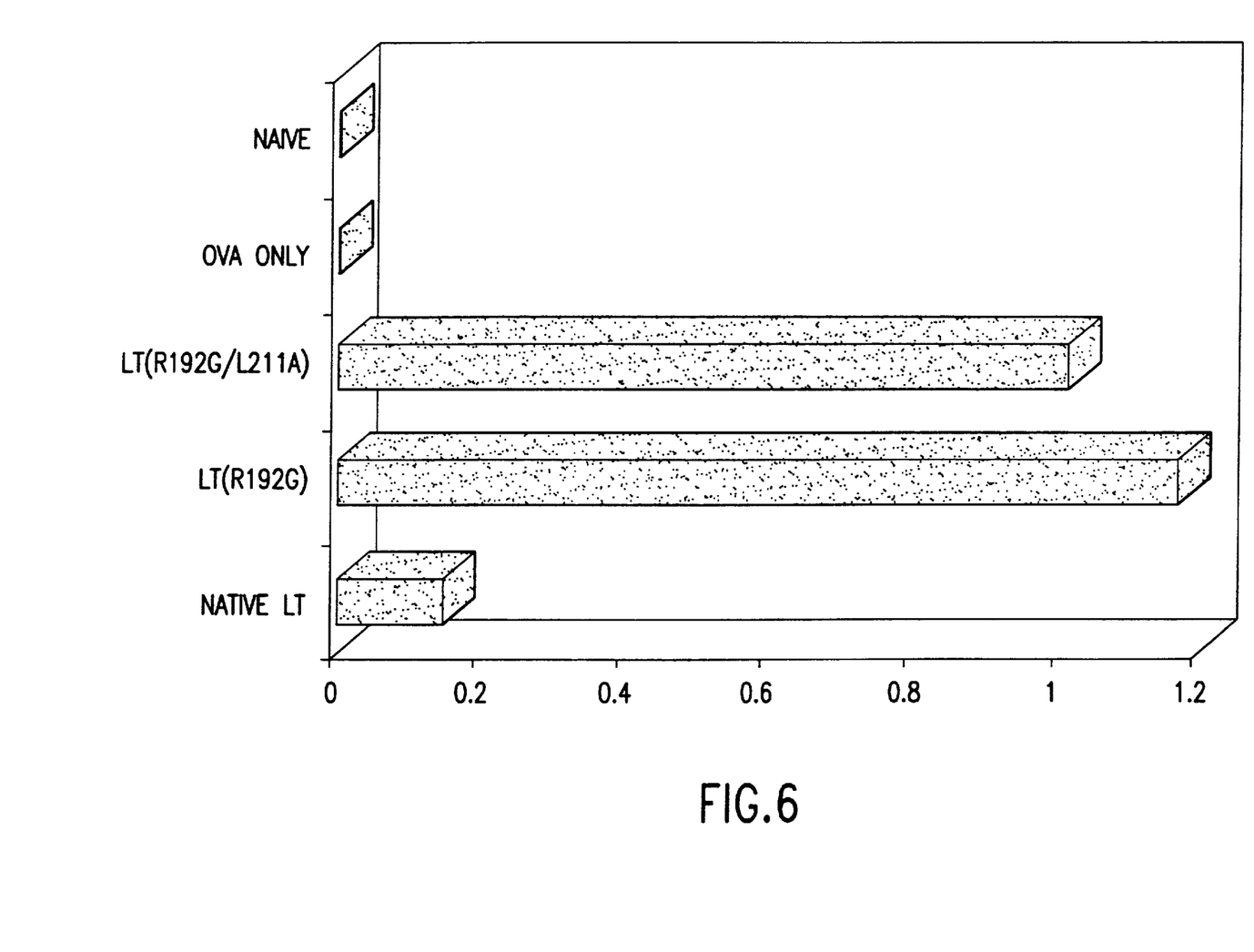
FIG. 6 is an experimental demonstration that LT(R192G/L211A) has the same ability as LT(R192G) to function as an immunologic adjuvant for production of antigen-specific Th2-type cytokines, specifically, IL-10, by mononuclear cells from the spleens of animals immunized intranasally. Mice were immunized intranasally with Ovalbumin (Ova) alone or in conjunction with 5 µg of LT(R192G) or LT(R192G/L211A). Cytokines were determined by ELISA following a T-cell restimulation assay. Mice immunized intranasally with Ova in conjunction with LT(R192G) had Ova-specific IL-10 responses indistinguishable from animals immunized with Ova in conjunction with LT(R192G/L211A).
Figure 7:
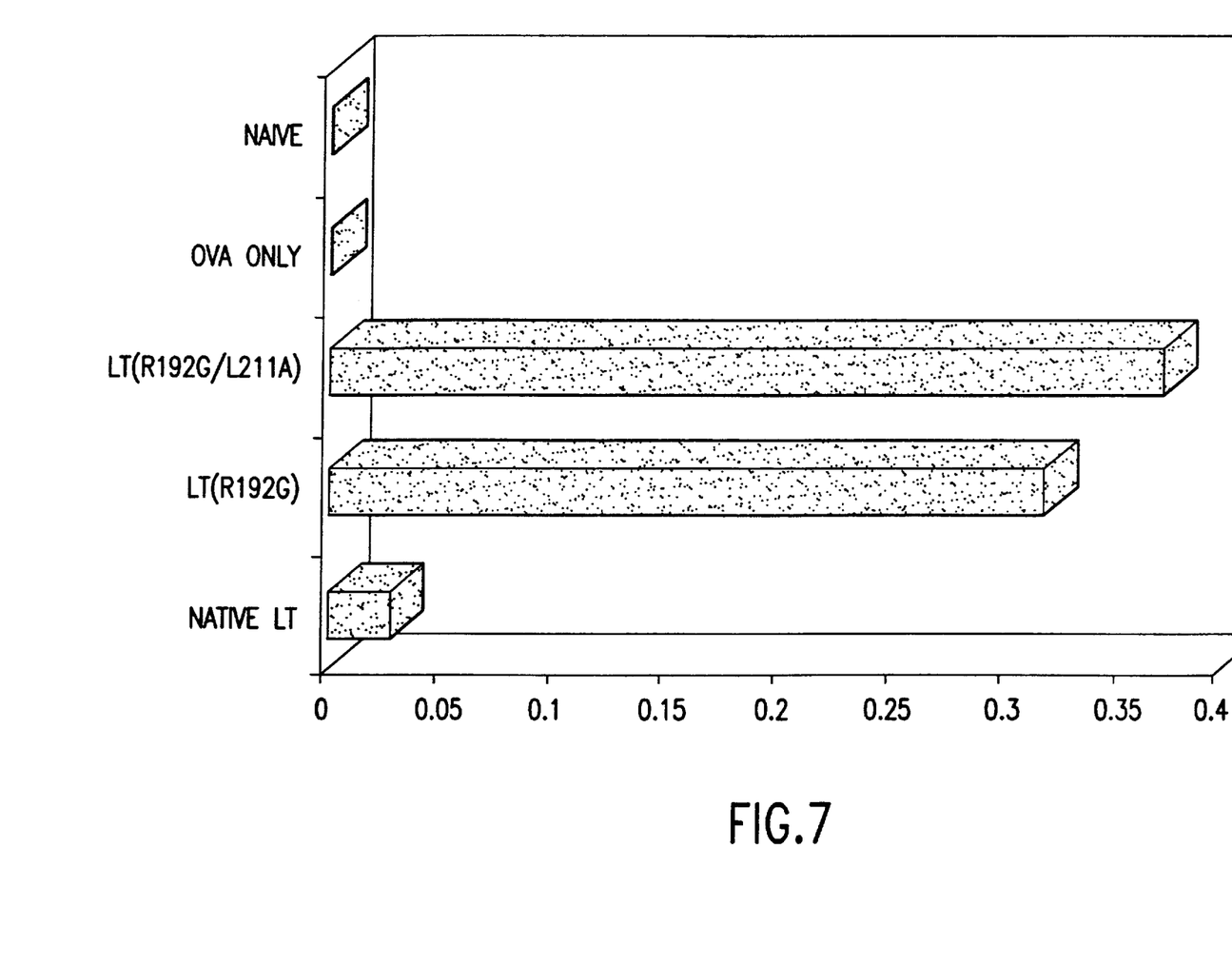
FIG. 7 is an experimental demonstration that LT(R192G/L211A) has the same ability as LT(R192G) to function as an immunologic adjuvant for production of antigen-specific Th2-type cytokines, specifically, IFN-gamma, by mononuclear cells from the spleens of animals immunized intranasally. Mice were immunized intranasally with Ovalbumin (Ova) alone or in conjunction with 5 µg of LT(R192G) or LT(R192G/L211A). Cytokines were determined by ELISA following a T-cell restimulation assay. Mice immunized intranasally with Ova in conjunction with LT(R192G) had Ova-specific IFN-gamma responses indistinguishable from animals immunized with Ova in conjunction with LT(R192G/L211A).

It has been surprisingly discovered that modifying the leucine at position 211 of LT(R192G) to alanine results in even lower enterotoxicity than LT(R192G), as measured in the patent mouse assay (see FIG. 4). The new molecule, referred to as LT(R192G/L211A), retains the adjuvanticity of LT(R192G), but exhibits even lower entertoxicity, in the patent mouse assay, than does LT(R192G).

The invention also provides a composition useful in the methods to stimulate an immune response. The composition comprises an effective amount of LT(R192G/L211A) in combination with an effective amount of antigen.

4. BRIEF DESCRIPTION OF THE FIGURES

The present invention may be understood more fully by reference to the following detailed description of the invention, examples of specific embodiments of the invention and the appended figures in which:

FIG. 1 is a schematic diagram of plasmid pCS95, which encodes both subunits LT A and B under the control of the lac promoter. FIG. 1A illustrates the construction of plasmid pCS95 which contains the nucleotide sequence encoding mutant LT(R192G). Plasmid pCS95 was constructed by replacing the BamHI-XbaI of pBD95 with the BamHI-XbaI fragment of pDF82. The lower half of FIG. 1B shows the single amino acid change in LT(R192G), encoded for by pCS95. The upper half of FIG. 1B shows the additional amino acid change in LT(R192G), which yields plasmid pECD401 coding for LT(R192G/L211A). Plasmid pECD401 provides LT(R192G/L211A) which contains two base substitutions, one at amino acid residue 192 of subunit A, coding for Gly rather than Arg, and another at amino acid residue 211 of subunit A, coding for Ala rather than Leu. All mutations were induced by site directed mutagenesis.

5. DETAILED DESCRIPTION OF THE INVENTION

The present invention provides a new LT molecule containing a glycine at position 192 in place of an arginine (R192G) and an additional mutation of leucine at position 211 to alanine (L211A) of the A subunit of LT and compositions thereof, and methods of using said compositions as an adjuvant.

The mutant LT(R192G) is shown to have reduced enterotoxicity in the patent mouse assay when compared to native LT (see FIG. 4). In a randomized, placebo-controlled, dose escalating study in adult volunteers, 0 of 24 volunteers showed adverse reactions to single oral doses of 2, 25, or 50 µg of LT(R192G). (Oplinger ML, Baqar S, Trofa A F, Clements J D, Gibbs P, Pazzaglia G, Bourgeois A L, Scott D A, 1997, Safety and Immunogenicity in Volunteers of a New Candidate Oral Mucosal Adjuvant, LT(R192G), Abstr. G-10, p. 193, In: Program and Abstracts of the 37th Interscience Conference on Antimicrobial Agents and Chemotherapy, American Society for Microbiology, Washington, D.C.). This is in contrast to native LT, which was shown to be enterotoxic at 2.5 µg in volunteers when combined with the B-subunit/Whole Cell Cholera vaccine. However, at 100 µg of LT(R192G), 2 of 12 (16.7%) of volunteers developed mild to moderate diarrhea which resolved within 24 hours.

The attenuating mutation in LT(R192G) is in the site where proteolytic activation by trypsin-like proteases is thought to occur in the native molecule, that is, the trypsin sensitive Arg residue within the region subtended by the disulfide loop of the A-subunit. Trypsin is not the only protease found in the mammalian intestinal tract. Pepsin is the principle proteolytic enzyme in gastric juice and functions optimally at acidic pH. Pepsin cleaves preferentially at peptide bonds involving the carboxylic groups of aromatic amino acids and other hydrophobic amino acids (especially phenylalanine and leucine). Pepsin will not cleave bonds containing a valine, alanine, or glycine. Within the region of LT distal to the trypsin cleavage site at position 192 lies a potential pepsin cleavage site, a leucine at position 211.

Using site directed mutagenesis, the leucine at position 211 of native LT and of LT(R192G) was replaced with an alanine residue, creating a single mutant LT(L211A) and the double mutant LT(R192G/L211A).

As shown in the Examples below (see section 6.2), the single mutant LT(L211A) retained the sensitivity to trypsin of native LT, while the double mutant LT(R192G/L211A) was insensitive to trypsin cleavage. This was expected since the single mutant LT(R192G) is not sensitive to trypsin cleavage. Unexpectedly, both the single and double mutants of LT as well as native LT were found to be resistant to pepsin cleavage. Thus, even though the leucine residue at position 211 is a potential pepsin cleavage site, it does not appear to function as such.

LT(R192G) has substantially reduced enterotoxicity when compared to native LT in the patent mouse assay. 250 µg of LT(R192G) has less enterotoxicity in the patent mouse model than does 5 µg of native LT. However, there is some amount of fluid accumulation. Surprisingly, even though the leucine residue at position 211 is not a pepsin cleavage site and LT(L211A) retains sensitivity to proteolytic cleavage by trypsin, the single mutant LT(L211A) has greatly reduced enterotoxicity as well, exhibiting approximately the same level of enterotoxicity as LT(R192G). The double mutant LT(R192G/L211A) has essentially no enterotoxicity in this assay (see FIG. 4).

5.1 LT(R192G/L211A) and Compositions Thereof

The present invention encompasses a composition and methods for its use to promote the production of serum and/or mucosal antibodies as well as cell-mediated immune responses against antigens that are simultaneously administered with a genetically modified bacterial toxin.

The modified toxin is a form of the heat-labile enterotoxin (LT) of *E. coli* which through modification of the arginine at position 192 to glycine and the modification of the leucine at position 211 to arginine, has lost the trypsin sensitive site joining the A1 and A2 subunits, rendering the molecule non-toxic but still able to act as an immunological adjuvant. The invention is based on the discovery that LT(R192G/L211A) has utility as an adjuvant for mucosally or parenterally administered antigens; such administration results in the production of serum IgG and/or mucosal sIgA as well as cell-mediated immune responses against the antigens with which LT(R192G/L211A) is delivered.

5.2 Production of LT(R192G/L211A)

LT(R192G/L211A) can be produced by a number of means apparent to those of skill in the art. For example, plasmid pECD403, fully described in Example 6.1, can be utilized to produce substantially pure LT(R192G/L211A) in *E. coli*. LT(R192G/L211A) can be isolated by agarose affinity chromatography from bacteria expressing an LT(R192G/L211A) encoding plasmid. Alternate methods of purification will be apparent to those skilled in the art.

5.2.1 Mode of Administration of LT(R192G/L211A) and Unrelated Antigens

In accordance with the present invention LT(R192G/L211A) can be administered in conjunction with any biologically relevant antigen and/or vaccine, such that an increased immune response to said antigen and/or vaccine is achieved. In one embodiment, LT(R192G/L211A) is a component of a vaccine directed against an enterotoxic bacterial organism.

In a preferred embodiment, the LT(R192G/L211A) and antigen are administered simultaneously in a pharmaceutical composition comprising an effective amount of LT(R192G/L211A) and an effective amount of antigen. The mode of administration is mucosal (i.e., intranasal, oral, rectal) or parenteral (i.e., subcutaneous, intramuscular, intradermal, intravenous, intraperitoneal).

In an alternate embodiment, the LT(R192G/L211A) and antigen are administered separately within a short time of each other.

The respective amounts of LT(R192G/L211A) and antigen will vary depending upon the identity of the route of administration, antigen employed and the species of animal to be immunized. In one embodiment, the initial administration of LT(R192G/L211A) and antigen is followed by a boost of the relevant antigen. In another embodiment no boost is given. The timing of boosting may vary, depending on the route, antigen and the species being treated. The modifications in route, dosage range and timing of boosting for any given species and antigen are readily determinable by routine experimentation. The boost may be of antigen alone or in combination with LT(R192G/R211A).

The present invention also provides for a kit useful in producing a protective immune response in a host to a pathogen, said kit comprising an effective amount of antigen and an adjuvant effective amount of a LT(R192G/L211A).

5.3 Antigens Useful in the Invention

The methods and compositions of the present invention are intended for use both in immature and mature vertebrates, in particular birds, mammals, and humans. Useful antigens, as examples and not by way of limitation, would include antigens from pathogenic strains of bacteria (*Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis,* Mycoplasma spp., *Rickettsia prowazeki, Rickettsia tsutsugumushi,* Chlamydia spp., *Helicobacter pylori*); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms) either presented to the immune system in whole cell form or in part isolated from media cultures designed to grow said organisms which are well know in the art, or protective antigens from said organisms obtained by genetic engineering techniques or by chemical synthesis.

Other relevant antigens would be pathogenic viruses (as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus) either presented to the immune system in whole or in part isolated from media cultures designed to grow such viruses which are well known in the art or protective antigens therefrom obtained by genetic engineering techniques or by chemical synthesis.

Further examples of relevant antigens include, but are not limited to, vaccines. Examples of such vaccines include, but are not limited to, influenza vaccine, pertussis vaccine, diphtheria and tetanus toxoid combined with pertussis vaccine, hepatitis A vaccine, hepatitis B vaccine, hepatitis C vaccine, hepatitis E vaccine, Japanese encephalitis vaccine, herpes vaccine, measles vaccine, rubella vaccine, mumps vaccine, mixed vaccine of measles, mumps and rubella, papillomavirus vaccine, parvovirus vaccine, respiratory syncytial virus vaccine, Lyme disease vaccine, polio vaccine, varicella vaccine, gonorrhea vaccine, schistosomiasis vaccine, rotavirus vaccine, mycoplasma vaccine pneumococcal vaccine, meningococcal vaccine, campylobacter vaccine, helicobacter vaccine, cholera vaccine, enterotoxigenic *E. coli* vaccine, enterohemmorgagic *E. coli* vaccine, shigella vaccine, salmonella vaccine and others. These can be produced by known common processes. In general, such vaccines comprise either the entire organism or virus grown and isolated by techniques well known to the skilled artisan or comprise relevant antigens of these organisms or viruses which are produced by genetic engineering techniques or chemical synthesis. Their production is illustrated by, but not limited to, as follows:

Influenza vaccine: a vaccine comprising the whole or part of hemagglutinin, neuraminidase, nucleoprotein and matrix protein which are obtainable by purifying a virus, which is grown in embryonated eggs, with ether and detergent, or by genetic engineering techniques or chemical synthesis.

Pertussis vaccine: a vaccine comprising the whole or a part of pertussis toxin, hemagglutinin and K-agglutinin which are obtained from avirulent toxin with formalin which is extracted by salting-out or ultracentrifugation from the culture broth or bacterial cells of *Bordetella pertussis*, or by genetic engineering techniques or chemical synthesis.

Diphtheria and tetanus toxoid combined with pertussis vaccine: a vaccine mixed with pertussis vaccine, diphtheria and tetanus toxoid.

Japanese encephalitis vaccine: a vaccine comprising the whole or part of an antigenic protein which is obtained by culturing a virus intracerebrally in mice and purifying the virus particles by centrifugation or ethyl alcohol and inactivating the same, or by genetic engineering techniques or chemical synthesis.

Hepatitis B vaccine: a vaccine comprising the whole or part of an antigen protein which is obtained by isolating and purifying the HBs antigen by salting-out or ultracentrifugation, obtained from hepatitis carrying blood, or by genetic engineering techniques or by chemical synthesis.

Measles vaccine: a vaccine comprising the whole or part of a virus grown in a cultured chick embryo cells or embryonated egg, or a protective antigen obtained by genetic engineering or chemical synthesis.

Rubella vaccine: a vaccine comprising the whole or part of a virus grown in cultured chick embryo cells or embryonated egg, or a protective antigen obtained by genetic engineering techniques or chemical synthesis.

Mumps vaccine: a vaccine comprising the whole or part of a virus grown in cultured rabbit cells or embryonated egg, or a protective antigen obtained by genetic engineering techniques or chemical synthesis.

Mixed vaccine of measles, rubella and mumps: a vaccine produced by mixing measles, rubella and mumps vaccines.

Rotavirus vaccine: a vaccine comprising the whole or part of a virus grown in cultured MA 104 cells or isolated from the patient's feces, or a protective antigen obtained by genetic engineering techniques or chemical synthesis.

Mycoplasma vaccine: a vaccine comprising the whole or part of mycoplasma cells grown in a liquid culture medium for mycoplasma or a protective antigen obtained by genetic engineering techniques or chemical synthesis.

Those conditions for which effective prevention may be achieved by the present method will be obvious to the skilled artisan.

The vaccine preparation compositions of the present invention can be prepared by mixing the above illustrated antigens and/or vaccines with LT(R192G/L211A) at a desired ratio. Pyrogens or allergens should naturally be removed as completely as possible. The antigen preparation of the present invention can be used by preparing the antigen per se and the LT(R192G/L211A) separately or together.

Further, the present invention encompasses a kit comprising an effective amount of antigen and an adjuvant effective amount of LT(R192G/L211A). In use, the components of the kit can either first be mixed together and then administered or the components can be administered separately within a short time of each other.

The vaccine preparation compositions of the present invention can be combined with either a liquid or solid pharmaceutical carrier, and the compositions can be in the form of tablets, capsules, powders, granules, suspensions or solutions. The compositions can also contain suitable preservatives, coloring and flavoring agents, or agents that produce slow release. Potential carriers that can be used in the preparation of the pharmaceutical compositions of this invention include, but are not limited to, gelatin capsules, sugars, cellulose derivations such as sodium carboxymethyl cellulose, gelatin, talc, magnesium stearate, vegetable oil such as peanut oil, etc., glycerin, sorbitol, agar and water. Carriers may also serve as a binder to facilitate tabletting of the compositions for convenient administration.

6. EXAMPLES

The following examples are presented for purposes of illustration only and are not intended to limit the scope of the invention in any way.

6.1. Construction of LT(R192G/L211A)

The wild-type LT toxin is encoded on a naturally occurring plasmid found in strains of enterotoxigenic *E. coli* capable of producing this toxin. Clements et al. had previously cloned the LT gene from a human isolate of *E. coli* designated H10407. This subclone consists of a 5.2 kb DNA fragment from the enterotoxin plasmid of H10407 inserted into the PstI site of plasmid pBR322 (Clements et al, 1983, *Infect. Immun.* 40:653). This recombinant plasmid, designated pDF82, has been extensively characterized and expresses LT under control of the native LT promoter. From pDF82, Clements et al. derived plasmid pBD95, which is fully described in PCT Publication WO96/06627.

Figure 1A:
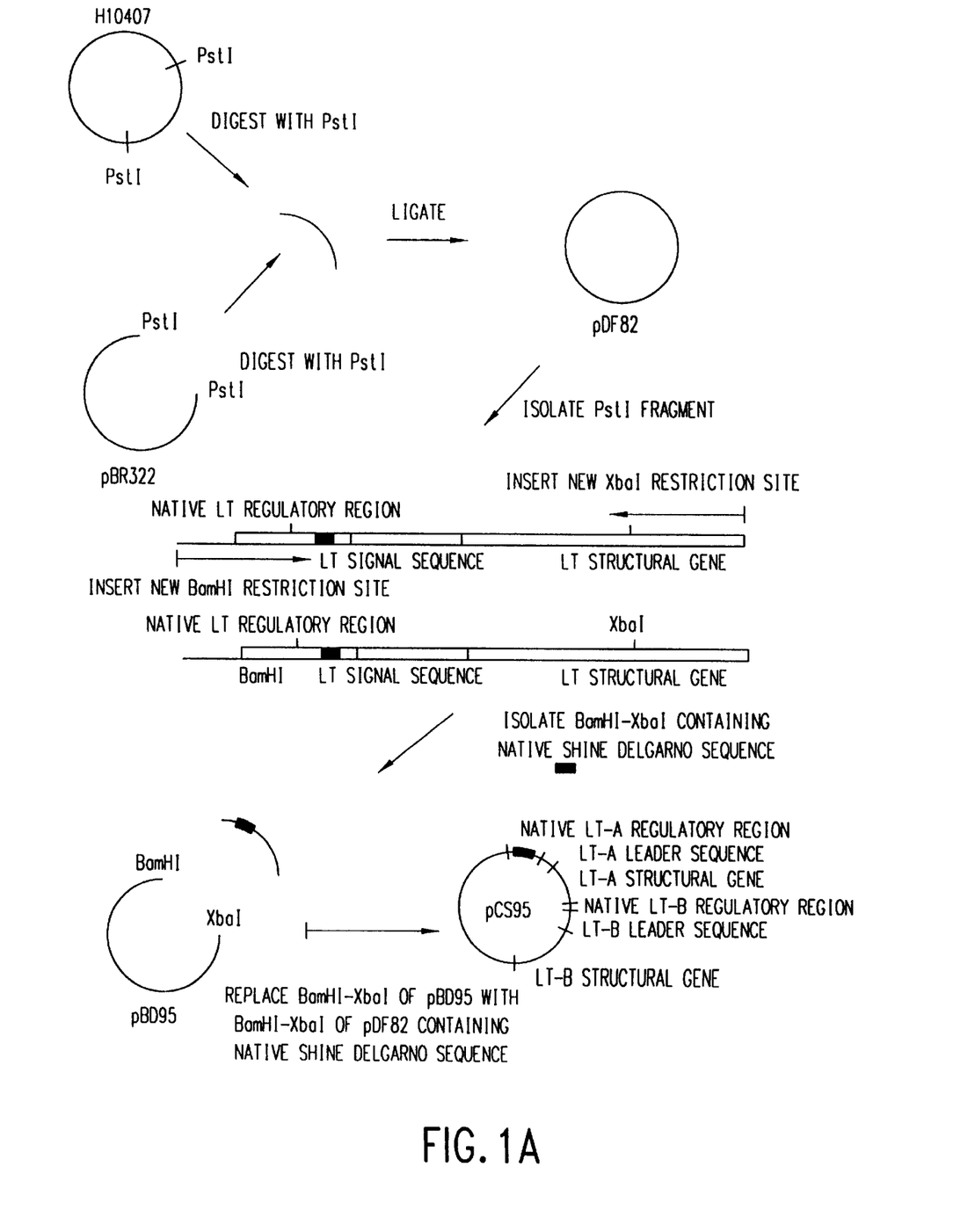
Figure 1B:
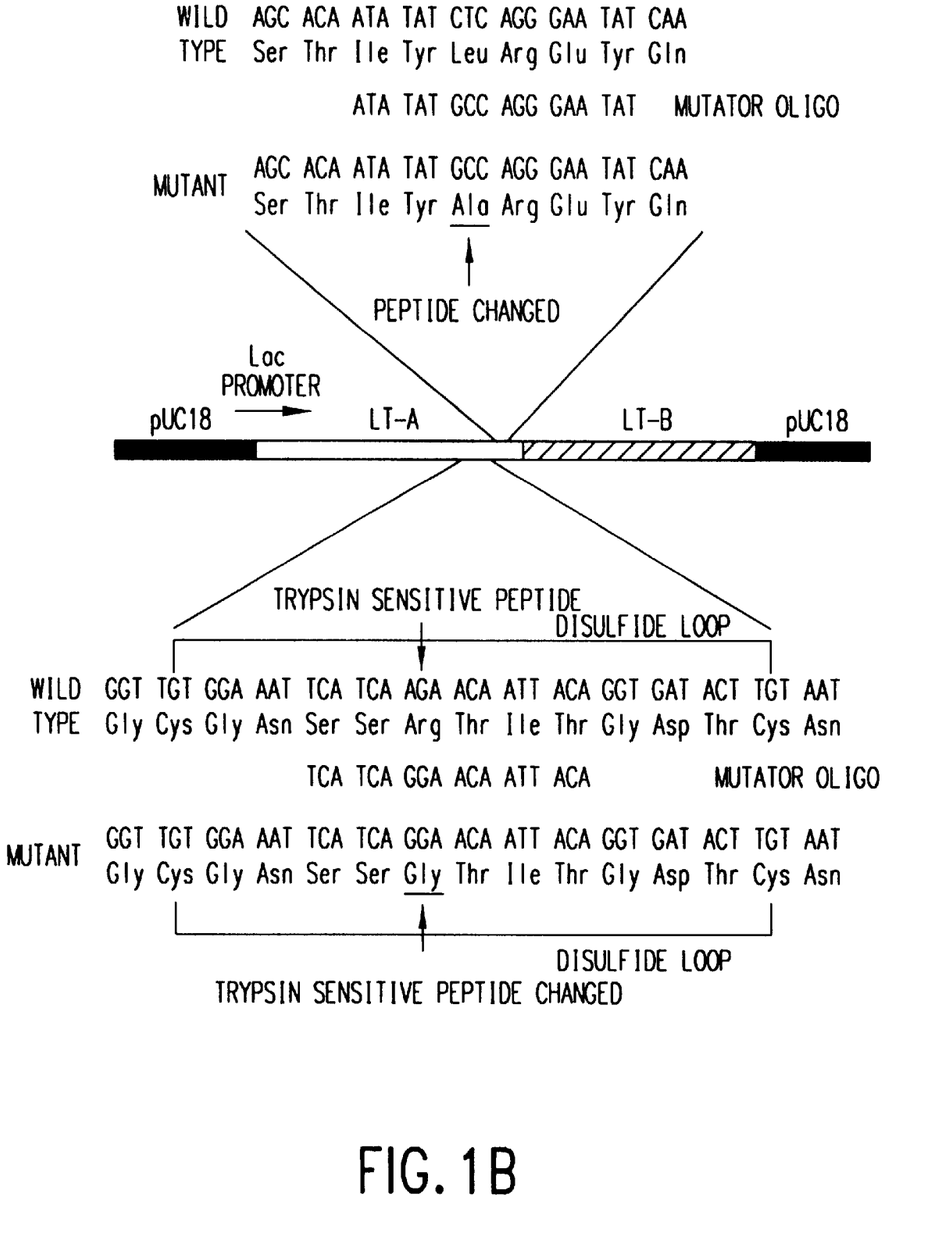
Figure 2:
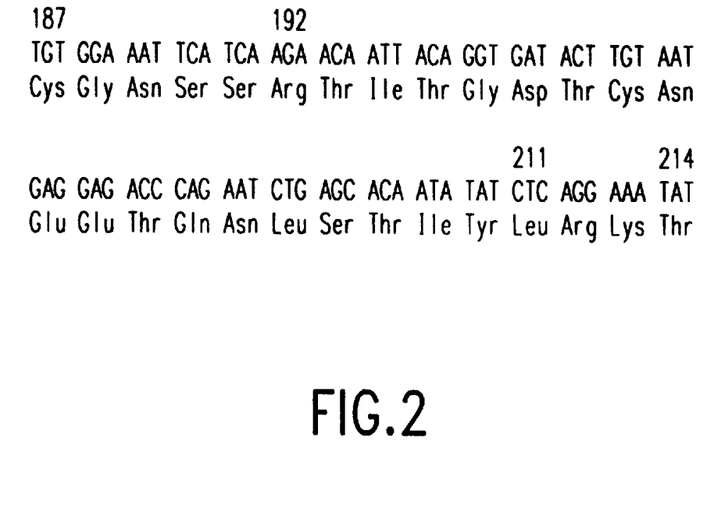
FIG. 2 shows a portion of the sequence of LT in the A-subunit, including a portion distal to the trypsin cleavage site at position 192 including the leucine at position 211.
Figure 3A:
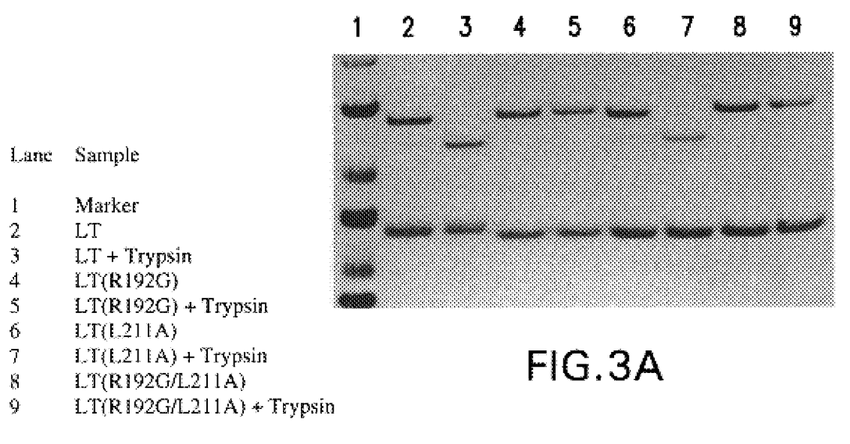
FIG. 3A and FIG. 3B show the sensitivity of wild-type LT and several LT mutants to trypsin and pepsin proteolysis.
Figure 3B:
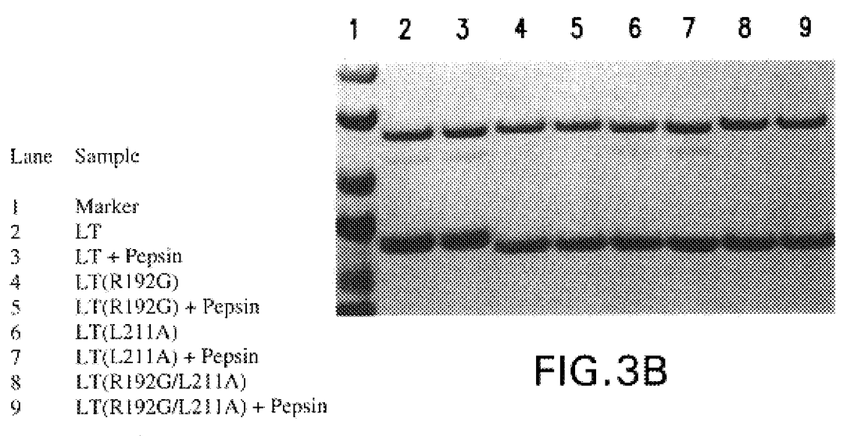

FIG. 1A shows the construction of plasmid pCS95, which was constructed by inserting the native LT-A subunit regulatory region upstream from the LT-A coding region of pBD95. FIG. 1B shows the Arg to Gly mutation at position 192. The BamHI and XbaI restriction sites referred to in the diagram as "new" were added by site directed mutagenesis, as described in PCT Publication WO96/06627. The new XbaI site was added through a silent mutation, resulting in no alteration of the amino acid sequence of the peptide encoded by the gene.

Then, starting with the single mutant plasmid pCS95, Ala was substituted for Leu at position 211 (i.e., GCC=Ala replaces CTC=Leu) by site directed mutagenesis. The resultant mutant LT was then purified by agarose affinity chromatography from bacteria expressing the mutated plasmid, named pECD403, which had been confirmed by sequencing.

This mutant LT, designated LT(R192G/L211A) was then examined by SDS-polyacrylamide gel electrophoresis for modification of the trypsin sensitive bond. Samples were examined with and without exposure to trypsin and compared with native (unmodified) LT. LT(R192G/L211A) does not dissociate into $A_1$ and $A_2$ when incubated with trypsin, thereby indicating that sensitivity to protease has been removed.

6.2. LT(R192G/L211A) Exhibits Resistance to Pepsin Cleavage

Using site directed mutagenesis, the leucine at position 211 of native LT and of LT(R192G) was replaced with an alanine residue, creating a single mutant LT(L211A) and the double mutant LT(R192G/L211A).

Following purification by galactose affinity chromatography, both of these constructs were examined by SDS-PAGE analysis. As shown in FIG. 3, the single mutant LT(L211A) retained the sensitivity to trypsin of native LT (compare upper panel lanes 1 and 2 with lanes 6 and 7) while the double mutant LT(R192G/L211A) was insensitive to trypsin cleavage (upper panel lanes 8 and 9). This was expected since the single mutant LT(R192G) is not sensitive to trypsin cleavage (upper panel lanes 4 and 5). Unexpectedly, both the single and double mutants of LT as well as native LT were found to be resistant to pepsin cleavage. Thus, even though the leucine residue at position 211 is a potential pepsin cleavage site, it does not appear to function as such.

6.3. Enterotoxicity in the Patent Mouse Assay

LT(R192G/L211A) and LT(L211A) were examined for enterotoxicity in the patent mouse assay. As can be seen in FIG. 4, LT(R192G) has substantially reduced enterotoxicity when compared to native LT in this assay. 250 $\mu$g of LT(R192G) has less enterotoxicity in the patent mouse model than does 5 $\mu$g of native LT. However, there is some small amount of fluid accumulation. Surprisingly, even though the leucine residue at position 211 is not a pepsin cleavage site and LT(L211A) retains sensitivity to proteolytic cleavage by trypsin, the single mutant LT(L211A) has greatly reduced enterotoxicity as well and approximately the same level of enterotoxicity as LT(R192G). The double mutant LT(R192G/L211A) has essentially no enterotoxicity in this assay.

6.4. Intranasal Adjuvanticity of LT(R192G/L211A)

Ovalbumin (Ova) was selected as a representative antigen for these studies. A number of investigations, including our own (Clements et al., 1988, *Vaccine* 6:269–277; Dickinson and Clements, 1996, *Mucosal Vaccines* :73–87; Dickinson and Clements, 1995, *Infection and Immunity,* 63:1617–1623; Tsuji et al., 1997, *Immunology* 90:176–182; Yamamoto et al., 1997, *Journal of Experimental Medicine* 185:1203–1210; Yamamoto et al., 1997, *Proceedings of the National Academy of Sciences* 94:5267–5272; DiTommaso et al., 1996, *Infection and Immunity* 64:974–979; Douce et al., 1995, *Proceedings of the National Academy of Sciences* 92:1644–1648; Douce et al., 1997, *Infection and Immunity* 65:2821–2828), have used this protein and it provides a useful and necessary reference for comparison to other studies. For those studies, both serum anti-Ova IgG and Ova-specific T-cell responses were examined.

Mice were immunized intranasally with Ova alone or in conjunction with 5 $\mu$g of LT(R192G) or LT(R192G/L211A). Serum anti-Ova IgG was determined by ELISA. There were seven animals per group and the means for each data point are shown. As shown in FIG. 5, mice immunized intranasally with Ova in conjunction with LT(R192G) had serum anti-Ova IgG responses indistinguishable from animals immunized with Ova in conjunction with LT(R192G/L211A). When the Ova-specific T-cell responses from these animals were examined, both the Th2/IL-10 (FIG. 6) and the Th1/IFN-gamma (FIG. 7) anti-Ova responses were equivalent when either LT(R192G) or LT(R192G/L211A) was used in the adjuvant formulation. There is no significant difference in the IFN-gamma and IL-10 responses between these two groups.

7. DEPOSIT OF PLASMIDS

The following plasmid was deposited with the American Type Culture Collection (ATCC), 10801 University Boulevard, Manassas, Va. 20110-2209 on Mar. 13, 1998, and has been assigned the indicated accession number:

| Plasmid | Accession Number |
|---|---|
| pECD403 | 98697 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosure of which are incorporated by reference in their entireties.

What is claimed is:

1. A composition comprising a mutant *E. coli* heat-labile enterotoxin holotoxin, in which arginine at amino acid position 192 is replaced with glycine and in which leucine at amino acid position 211 is replaced with alanine, which holotoxin has immunologic adjuvant activity and is:

(a) substantially less toxic than native *E. coli* heat-labile enterotoxin holotoxin as measured in the Y-1 adrenal cell assay, (b) substantially less toxic than native *E. coli* heat-labile enterotoxin holotoxin as measured in the patent mouse assay, and (c) less toxic than a composition consisting of isolated LT(R192G) as measured in the patent mouse assay.

2. The composition of claim 1 in which the holotoxin is encoded by a plasmid contained in *E. coli* having ATCC Accession number 98697.

3. A preparation comprising an antigen in combination with the composition according to claim 1.

4. The preparation according to claim 3, in which the antigen is selected from the group consisting of bacterial, fungal, protozoal, viral, helminthal and other microbial antigens.

5. The preparation according to claim 4, in which the antigen is from a microbe selected from the group consisting of *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromatis, Staphylococcus aureus, Vibrio cholerae, Escherichia coli, Pseudomonas aeruginosa, Campylobacter* (Vibrio) *fetus, Campylobacter jejuni, Aeromonas* hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma spp., Rickettsia prowazeki, Rickettsia tsutsugamushi, Chlamydia spp., Helicobacter pylori, Coccidioides immitis, Aspergillus fumigatus, Candida albicans, Blastomyces dermatitidis, Cryptococcus neoformans, Histoplasma capsulatum, Entamoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Enterobius vermicularis, Trichuris trichiura, Ascaris lumbricoides, Trichinella spiralis, Strongyloides stercoralis, Schistosoma japonicum, Schistosoma mansoni, Schistosoma haematobium, variola virus, vaccinia virus, cowpox virus, varicella-zoster virus, Herpes Simplex virus 1, Herpes Simplex virus 2, influenza viruses, parainfluenza virus, mumps virus, measles virus, respiratory syncytial virus, rubella virus, Hepatitis A virus, Hepatitis B virus, Hepatitis C virus, Hepatitis E virus, and Non-A/Non-B Hepatitis virus.

6. A composition useful in producing an immune response to a pathogen in a host comprising an admixture of an effective amount of an antigen and an adjuvant effective amount of the composition according to claim 1.

7. A kit useful in producing an immune response in a host to a pathogen comprising two components: (a) an effective amount of antigen and (b) an adjuvant effective amount of a mutant E. coli heat-labile enterotoxin holotoxin, in which arginine at amino acid position 192 is replaced with glycine and in which leucine at amino acid position 211 is replaced with alanine, which holotoxin has immunologic adjuvant activity and is:

(a) substantially less toxic than native E. coli heat-labile enterotoxin holotoxin as measured in the Y-1 adrenal cell assay, (b) substantially less toxic than native E. coli heat-labile enterotoxin holotoxin as measured in the patent mouse assay, and (c) less toxic than a composition consisting of isolated LT(R192G) as measured in the patent mouse cell assay.

8. A method of creating or sustaining an immune response to an antigen in a host comprising orally administering an admixture of an effective amount of an antigen and an adjuvant effective amount of a mutant E. coli heat-labile enterotoxin holotoxin, in which arginine at amino acid position 192 is replaced with glycine and in which leucine at amino acid position 211 is replaced with alanine, which holotoxin is substantially less toxic than native E. coli heat-labile enterotoxin holotoxin as measured in the Y-1 adrenal cell assay, substantially less toxic than native E. coli heat-labile enterotoxin holotoxin as measured in the patent mouse assay, and less toxic than compositions of isolated LT(R192G) as measured in the patent mouse assay, in an orally acceptable pharmaceutical carrier.

9. The method of claim 8 where a serum immune response is produced.

10. The method of claim 8 where a cell-mediated immune response is produced.

11. The method of claim 8 where a mucosal immune response is produced.

12. The method of claim 8 further comprising administering a subsequent boost of the antigen.

13. The method of claim 8 wherein the antigen is from a microbe derived from the group consisting of bacteria, viruses, protozoa, fungi, helminths, and other microbial pathogens.

14. A method of inducing an immune response to an antigen in a host comprising orally administering an effective amount of an antigen in conjunction with an adjuvant effective amount of a mutant E. coli heat-labile enterotoxin holotoxin, in which arginine at amino acid position 192 is replaced with glycine and in which leucine at amino acid position 211 is replaced with alanine, which holotoxin has immunologic adjuvant activity and is:

(a) substantially less toxic than native E. coil heat-labile enterotoxin holotoxin as measured in the Y-1 adrenal cell assay, (b) substantially less toxic than native E. coli heat-labile enterotoxin holotoxin as measured in the patent mouse assay, and (c) less toxic than a composition consisting of isolated LT(R192G) as measured in the patent mouse assay.

15. The method of claim 14 in which the antigen and the holotoxin are administered simultaneously.

16. The method of claim 14 in which the antigen and holotoxin are administered separately.

17. A method of inducing an immune response against an enterotoxic bacterial organism comprising administering a mutant E. coli heat-labile enterotoxin holotoxin, in which arginine at amino acid position 192 is replaced with glycine and in which leucine at amino acid position 211 is replaced with alanine, which holotoxin has immunologic adjuvant activity and is:

(a) substantially less toxic than native E. coli heat-labile enterotoxin holotoxin as measured in the Y-1 adrenal cell assay, and (b) less toxic than a composition consisting of isolated LT(R192G) as measured in the patent mouse assay, as a component of a vaccine directed against the enterotoxic bacterial organism.

18. The method of claim 17 wherein the enterotoxic bacterial organism is selected from the group consisting of enterotoxic bacterial organisms which express a cholera-like toxin.

19. The method of claim 17 wherein the enterotoxic bacterial organism is selected from the group consisting of Escherichia spp. and Vibrio spp.

* * * * *